[19] United States Patent
Blaser

[11] 4,290,429
[45] Sep. 22, 1981

[54] BATTERY MONITORING CIRCUIT IN A CARDIAC PACEMAKER

[75] Inventor: Reinhard Blaser, Büdingen, Fed. Rep. of Germany

[73] Assignee: Biotronick Mess-und Therapiegeräte GmbH & Co. Ingenieurbüro Berlin, Berlin, Fed. Rep. of Germany

[21] Appl. No.: 136,094

[22] Filed: Mar. 31, 1980

[30] Foreign Application Priority Data

Mar. 31, 1979 [DE] Fed. Rep. of Germany ....... 2913399

[51] Int. Cl.$^3$ ............................................. A61N 1/36
[52] U.S. Cl. ............................................. 128/419 PT
[58] Field of Search .................. 128/419 PG, 419 PS, 128/419 PT

[56] References Cited

U.S. PATENT DOCUMENTS

| | | | |
|---|---|---|---|
| 3,866,614 | 2/1975 | Svensson | 128/419 PG |
| 4,015,609 | 4/1977 | Mensinic et al. | 128/419 PS |
| 4,031,899 | 6/1977 | Renirie | 128/419 PS |
| 4,124,031 | 11/1978 | Mensink et al. | 128/419 PT |

Primary Examiner—William E. Kamm

Attorney, Agent, or Firm—Spencer & Kaye

[57] ABSTRACT

In a monitoring circuit for monitoring the state of the battery of a cardiac pacemaker, which pacemaker includes an energy storage element normally connected to be charged by the battery and to constitute an energy source for the pacemaker components, the circuit including a voltage detector connected to emit a signal when a parameter representative of the battery state passes a threshold value, the circuit further includes: first switching member for disconnecting the battery from the energy storage element during periodically recurring time periods of given duration; a fixed load having an impedance which is large compared to the internal resistance of the battery and connected to apply to the voltage detector a voltage representative of the current flowing through the fixed load; an element for connecting the load across the battery during each time period for causing the load to be supplied with a current having a value at least indirectly defining the parameter representative of the battery state; and a storage member connected to provide an indication of the emission of such signal by the voltage detector.

7 Claims, 8 Drawing Figures

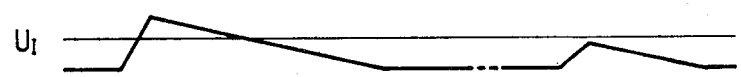
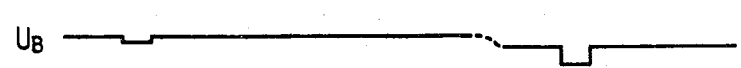
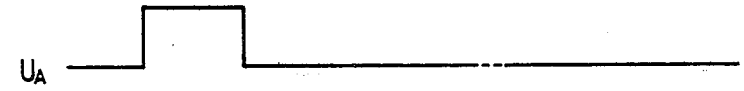

BATTERY MONITORING CIRCUIT IN A CARDIAC PACEMAKER

BACKGROUND OF THE INVENTION

The present invention relates to a circuit for monitoring the state of battery in a cardiac pacemaker, particularly a circuit of the type including a voltage detector which emits a signal as soon as a value characterizing the battery state passes a threshold.

In artificial cardiac pacemakers, such circuits serve to indicate the approaching end of the operating life (EOL) of the battery so that the necessary measures can be taken in time. A widespread way of achieving this is by constructing the generator of the cardiac pacemaker, which generates stimulation pulses, to have a frequency characteristic which is such that its pulse rate has a fixed value during normal operation and decreases with decreasing battery voltage. Once the pulse rate drops below a given value, replacement of the battery is necessary.

When CMOS circuits or quartz controlled oscillators are used to determine the stimulation pulse rate, their frequency does not change noticeably with a change in the battery voltage. To nevertheless obtain an indication of the battery state it is known to provide additional voltage dependent trigger circuits in the circuitry of cardiac pacemakers with the additional circuits emitting a signal when the battery voltage drops below a given value. These known circuits evaluate only the terminal voltage of the battery. However, due to the internal resistance of the battery, the terminal voltage existing when the battery load is drawing current depends on the current consumption necessitated by the particular operating state of the pacemaker. Since, in particular, programmable pacemakers have widely varying operating behaviors, the corresponding current consumption fluctuates considerably. Even with the conventional demand pacemakers, current consumption changes at a ratio of 5:1 during transition from inhibited to stimulating operation.

In a borderline region toward the end of the operating life of the battery it may then happen that in one mode of operation the approaching end of the battery life is already being indicated while this is not yet the case in the other mode of operation. This presents the danger that if the pacemaker continues to operate for a longer period of time in a relatively inactive mode, nothing indicates the approaching exhaustion of the battery so that if, as a result of cardiac behavior, a longer phase of operation with greater pacemaker activity is required, the end of the operating life of the battery, although an appropriate warning signal is emitted, may be reached dangerously quickly since during the preceding mode of operation the battery charge had already been depleted to too great an extent without this having been noticed.

If the signal emitted by such a circuit to monitor the battery state is used to reduce the basic rate of the oscillator, which is generally independent of the operating voltage, by internal switching, the average current consumption of the pacemaker is reduced and the battery terminal voltage, which has been smoothed by filter members increases again. Thus the control circuit will no longer emit a signal and the basic rate of the pacemaker will be stepped up again. This feedback effect therefore produces a continuous change in frequency which is extremely annoying for the user of the pacemaker.

SUMMARY OF THE INVENTION

It is an object of the invention to provide a pacemaker battery monitoring circuit which provides an indication of the battery state independent of the momentary mode of operation of the pacemaker.

A further object of the invention is to provide a monitoring circuit which is adaptable to various types of batteries so that those events which indicate the approaching end of the operating life of the particular type of battery are safely detected and evaluated in every case.

These and other objects are achieved, according to the invention, in a monitoring circuit for monitoring the state of the battery of a cardiac pacemaker, which pacemaker includes an energy storage element normally connected to be charged by the battery and to constitute an energy source for the pacemaker components, the circuit including a voltage detector connected to emit a signal when a parameter representative of the battery state passes a threshold value, by further providing the monitoring circuit with: first switching means for disconnecting the battery from the energy storage element during periodically recurring time periods of given duration; means defining a fixed load having an impedance which is large compared to the internal resistance of the battery and connected to apply to the voltage detector a voltage proportional to the current flowing through the fixed load; second switching means for connecting the load across the battery during each time period for causing the load to be supplied with a current having a value at least indirectly defining the parameter representative of the battery state; and storage means connected to provide an indication of the emission of such signal by the voltage detector.

In circuits according to the present invention it is of particular advantage that it is not only the drop in the terminal voltage of the battery which is recognized as a sign of its imminent exhaustion, but the internal resistance of the battery is also used as a criterion, while changes in current consumption of the pacemaker circuit as a result of different modes of operation do not play a part. In this way it is possible to immediately detect even an unacceptable increase of the internal resistance of the battery which occurs only rarely, and, as a consequence to actuate an attention-calling signal without there first having to occur a battery state which causes the terminal voltage as well to drop below the threshold value due to an operating state with increased current consumption. A case is quite conceivable in which the internal resistance of the battery has already increased to such an extent that such an operating state with increased current consumption cannot be maintained at all.

In the circuit according to the present invention the means for effectively disconnecting and reconnecting the battery are preferably controlled by a single signal, with the battery connection being switched at defined points in time.

BRIEF DESCRIPTION OF THE DRAWING

FIGS. 2a–2g are waveforms illustrating the time sequences of the voltages at various points in the circuit according to FIG. 1.

DESCRIPTION OF THE PREFERRED EMBODIMENTS

Figure 1:
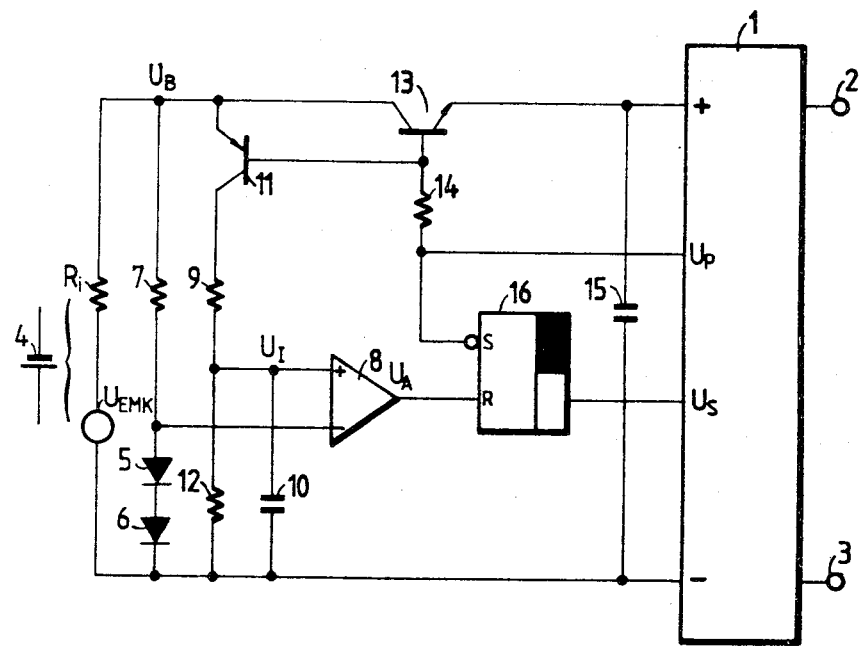
FIG. 1 is a circuit diagram of a preferred embodiment of a circuit according to the invention.

In the circuit shown in FIG. 1, the actual circuit of the pacemaker for generating stimulation pulses is shown as a whole as block 1. Any suitable, known stimulation pulse generating circuit can be employed, it only being necessary to select a power source providing the voltage and current levels required by the particular pacemaker. Terminals 2 and 3 serve as connection points for the transmission of signals to and from the heart.

The portion of the pacemaker circuit shown in detail to the left of block 1 includes a battery 4 forming the current supply and supplying a voltage $U_B$ between its terminals. The battery is represented in the circuit as a voltage source $U_{EMK}$ and a resistance $R_i$ representing the battery internal resistance. The components disposed between the battery 4 and the block 1 constitute the circuit according to the invention for monitoring the battery state.

Two diodes 5 and 6 are connected in series-aiding to be conductive in their forward direction and are connected in series with a resistor 7 across the battery terminals. Battery current thus flows through this series arrangement and diodes 5 and 6 together form a constant voltage source. Since the operating temperature of the pacemaker is essentially kept constant by the user's body temperature, means for temperature compensation are not required in this circuit, provided that the circuit is designed or dimensioned for operation at 37° C. The voltage across diodes 5 and 6 is applied to the inverting input of a differential amplifier 8 whose noninverting input receives a voltage $U_I$ which appears at the output of an integrator constituted by an RC member formed of a resistor 9 and a capacitor 10. At predetermined times, the RC member is connected to receive the terminal voltage $U_B$ of the battery 4 via the collector-emitter path of a transistor 11. When the transistor 11 is blocked, i.e. non-conductive, the capacitor 10 is discharged via a resistor 12 which has a resistance that is high compared to the resistance of resistor 9. The dimensions of the RC member are selected under consideration of operation of the circuit described below.

Together with the transistor 11 a further transistor 13 is actuated by a signal supplied to the bases of both transistors via a resistor 14. However this transistor 13 is of the opposite polarity type from transistor 11 so that the two transistors exhibit mutually opposite switching behavior in response to a given actuation signal. Instead of transistors 11 and 13, use can be made of other circuit elements which selectively act in a blocking and conductive manner.

Transistor 13 has its collector-emitter path connected between block 1 containing the actual stimulation circuit of the pacemaker, and the filter means for the supply voltage, which in the illustrated embodiment is a capacitor 15, on the one hand, and battery 4, on the other hand. Blocking of transistor 13 effectively disconnects battery 4 from units 1 and 15. Transistors 11 and 13 are actuated by pulse-type output voltage $U_p$, with the pulses actuating transistors 11 and 13 advisably being derived from the circuit 1.

If circuit 1 includes a CMOS circuit or some other digital circuit, a suitable pulse voltage $U_p$ can be derived from the available pulse generator circuits therein. Each monitoring period can be acutated by stimulation or clock pulses, respectively. The only prerequisites are that transistor actuating pulses have constant time durations and a repetition rate which assures sufficiently frequent checking of the battery.

The pulsating voltage $U_p$ is also applied to the setting input S of an RS flipflop 16 whose reset input R is connected to receive the voltage $U_A$ appearing at the output of the differential amplifier 8. The signal voltage $U_S$ appearing at the output of the RS flipflop is supplied to an input of block 1 where a signal is actuated, if flipflop 16 is set, which indicates the approaching end of the battery service life. To indicate this state the basic rate of the pacemaker may be reduced, for example as in the prior art pacemaker circuits, so that the person carrying the pacemaker or the attending physician has his attention called to the state of the battery. In a digitally designed pulse generator, the basic rate is reduced, for example, when the pulse generator reaches a given counter state and is thus set back to a starting state by appropriately influencing the logic comparison signals.

The operation of the circuit will now be described with the aid of the voltage waveform curves shown in FIG. 2, representing signal voltages appearing in the circuit of FIG. 1.

The pulse voltage $U_p$ determines the testing periods for the battery. These periods of time are correlated with stimulation pulses or are controlled by other timing means in such a way that they occur with sufficient frequency. When the voltage $U_p$ is at its positive maximum value, it maintains the transistor 13 conductive via its base and resistor 14. The value of voltage $U_p$ must then lie above the value of the positive supply voltage + of the block 1, which can be realized, for example by a voltage multiplying circuit of the type usually provided in pacemaker circuits. Transistor 11 is at the same time initially blocked. If a negative pulse appears in the course of voltage $U_p$, the transistor 13 is blocked and instead the transistor 11 becomes conductive because of the current now flowing through resistor 14 to its base terminal. At the same time, the flipflop 16 is set by application of the negative pulse to its inverting setting input S. When transistor 11 becomes conductive capacitor 10 is charged via resistor 9 the current flowing off through resistor 12 being negligible. The voltage $U_I$ across capacitor 10 increases during the negative pulse as can be seen in the diagram of FIG. 2b. The RC combination then constitutes a load for the battery 4 which is large compared to its internal resistance $R_i$.

The filter capacitor 15 is unable to furnich current to the battery or the integrator at this time since the blocked transistor 13 disconnects it from the battery 4. Even with a new battery, the internal resistance $R_i$ is greater than zero so that during the negative pulse period T the terminal voltage $U_B$ will exhibit a dip as shown at the left-hand side of FIG. 2c, which depicts the battery terminal voltage. With a sufficiently fresh battery, the peak of voltage $U_I$ across the capacitor 10 will exceed the value of the total voltage drop across diodes 5 and 6, the latter being represented by the horizontal line in the diagram for $U_I$ in FIG. 2b, so that at the inverting output of the differential amplifier 8 there is produced a rising pulse edge in voltage $U_A$, as shown in FIG. 2f, which resets the flipflop 16. The signal voltage $U_S$ appearing at the output of flipflop 16 will thus have taken on the logic 1, or high level, for no longer than the duration of the negative pulse of voltage $U_p$, so that no permanent signal state occurs to indicate the impending end of the service life of the battery. The "variable" region of the signal voltage $U_S$ is shown in the drawing by way of hatching.

The time duration of the variable pulses appearing within $U_S$ may vary from a very short duration, with a fresh battery to a duration approximating that of the pulses within $U_p$ towards the end of the battery's service life, when the leading edges of the pulses of the output of operational amplifier 8, resetting flipflop 16, nearly coincide with the trailing edges of the (negative) "test pulses" within $U_p$. (Thus the duration of the pulses within $U_S$ may be used as an indication of the battery condition until the end-of-life indication is actuated.) This will become more obvious from the following description.

With increasing length of operation of the battery the open-circuit voltage $U_{EMK}$ will generally drop and the internal resistance $R_i$ will rise. The result is that during the negative testing pulse period T in voltage $U_p$, the voltage $U_I$ across the capacitor will not exceed the threshold voltage drop across diodes 5 and 6, as shown at the right-hand portion of the voltage curves of FIGS. 2b and c. In that case the flipflop 16, although it is set by the descending edge of a pulse in voltage $U_P$, is no longer reset since the output voltage $U_A$ of the differential amplifier 8 does not change during the duration of the testing pulse. The voltage $U_S$ retains its high level and thus indicates the approaching end of the battery service life and this signal can be made to actuate suitable switching states within the remainder of the pacemaker circuit.

The end of the service life of a primary energy source can be determined, on the one hand, in that the operating voltage is reduced due to consumption of the material which reacts for producing the energy. On the other hand the capability of the battery to operate is also limited by the fact that reaction products are deposited at its electrodes and thus contribute to the increase in its internal resistance $R_i$. Generally, the reduction in the open-circuit voltage will coincide, as a result of the related chemical reactions, with a corresponding increase in the terminal voltage $U_B$ under test conditions will have the shape shown in the right-hand portion of FIG. 2c, where on the one hand, the no-load, i.e. open-circuited, terminal voltage is reduced, and, on the other hand, the additional dip under load is greater compared to the fresh state.

It may happen now that because a battery is faulty, the internal resistance $R_i$ already increases to an unacceptable degree before the normally expected end of its operating life. This change in the internal resistance cannot be detected by the normal, no load voltage measurement at the battery to determine the operating state. However, the curve shown in FIG. 2d with respect to a voltage $U_B''$ representing such a case shows that even with unchanging open-circuit voltage, the greater voltage dip in the right-hand portion of that Figure as a result of the increase in the internal resistance $R_i$ is sufficient to prevent the capacitor 10 from being charged beyond the threshold voltage of diodes 5 and 6 during the testing pulse.

If, on the other hand, only the no load voltage $U_{EMK}$ drops noticeably during operation without the internal resistance $R_i$ having increased correspondingly, this state, which is shown in the right-hand portion of FIG. 2e for a voltage $U_B'''$, will also be reliably detected since during the test pulse the terminal voltage $U_B''$ under load will have reached the minimum value at which the capacitor 10 will no longer charge sufficiently to generate a pulse of voltage UA. consideration of the resistance of resistor 12 and the pulse duration T, with regard to the battery type intended for the respective pacemaker, to assure that the signal indicating the approaching end of the service life of the battery will be reliably actuated, if, on the other hand, only the terminal voltage $U_{EMK}$ drops to its minimum permissible value and the internal resistance $R_i$ corresponds to that of a fresh battery, or on the other hand, only the internal resistance $R_i$ is increased to its permissible threshold value and the initial open circuit voltage $U_{EMK}$ is still present.

This assures that even if intermediate values occur the EOL indication for the battery will be given when it corresponds to the actual conditions, particularly if at the voltage to be evaluated by the voltage detector the increasing internal resistance and the decreasing open circuit voltage essentially linearly overlap. The exponential curve of the charging voltage for capacitor 10 and the changes resulting from the operational parameters of the battery can then be considered to be sufficiently linear in their initial portions, provided that the comparison voltage, i.e. the threshold voltage of diodes 5 and 6, is sufficiently low and the load resistance offered by components 9, 10, and 12 when transistor 11 is conductive is sufficiently high.

In an exemplary embodiment of the invention the components used are of the following values:

| | | |
|---|---|---|
| 7 | 8.9 M | |
| 9 | 47 k | |
| 12 | 8.9 M | |
| 14 | 100 k | |
| capacitors: | | |
| 10 | 47 n | |
| 15 | 33 μ | |
| diodes: | | |
| 5, 6 | D 875 | |
| operational amplifier: | | |
| 8 | 24 250 | |
| flipflop: | | |
| 16 | 4013 | with the inverting function of the "set"-input realized by an inverter 4011 |
| transistors: | | |
| 11, 13 | | replaced by switching devices 4066 |

With an embodiment including the components dimensionsed as specified a voltage drop of a new battery $(U_{EMK})_{BOL}$ of 5 volts to a voltage $(U_{EMK})_{EOL}$ of 4 volts has the same effect as an increase of the internal resistance $R_i$ of the battery from a low value—when new—to a value of 10 kiloohms at end-of-life condition, when the pulse width of $U_P$ is about 500 μs. The repetition rate of $U_P$ is correlated with that of the stimulation pulses of the pacemaker in a fixed frequency mode, which is about 535 ms. The input of $U_S$ of the pacemaker 1 is connected to a circuit component within the pacemaker circuit effecting a reduction of the fixed frequency rate indicative of the EOL-condition of the battery when flipflop 16 is set. The entrances + and − are providing the current supply of the pacemaker circuit.

It will be understood that the above description of the present invention is susceptible to various modifications, changes and adaptations, and the same are intended to be comprehended within the meaning and range of equivalents of the appended claims.

What is claimed is:

1. In a monitoring circuit for monitoring the state of the battery of a cardiac pacemaker, which pacemaker includes an energy storage element normally connected to be charged by the battery and to constitute an energy source for the pacemaker components, the circuit including a voltage detector connected to emit a signal when a parameter representative of the battery state passes a threshold value, the improvement comprising: first switching means for disconnecting the battery from the energy storage element during periodically recurring time periods of given duration; means defining a fixed load having an impedance which is large compared to the internal resistance of the battery and connected to apply to said voltage detector a voltage representative of the current flowing through said fixed load; means for connecting said load across the battery during each said time period for causing said load to be supplied with a current having a value at least indirectly defining the parameter representative of the battery state; and storage means connected to provide an indication of the emission of such signal by said voltage detector.

2. An arrangement as defined in claim 1 wherein the impedance of said fixed load has a value selected for causing the value of the current therethrough during each said time period to be less than that corresponding to the parameter threshold value when the battery reaches a state at which at least one of the following conditions exists: its open-circuit voltage is less than a minimum acceptable value for an internal resistance value equal to that of a fresh battery; and its internal resistance is greater than a maximum acceptable value for an open-circuit voltage value equal to that of a fresh battery.

3. An arrangement as defined in claim 1 wherein said fixed load comprises a capacitor and said means for connecting said load comprise second switch means connected for causing said capacitor to be charged by the current through said fixed load during a fixed time interval within each said time period and to apply a voltage proportional to its charge to said voltage detector.

4. An arrangement as defined in claim 3 wherein said storage means comprise a flipflop connected to be set at the beginning of each said time period and to be reset when said voltage detector emits a signal during said time period.

5. An arrangement as defined in claim 3 or 4 wherein each said fixed time interval coincides with a respective said time period.

6. An arrangement as defined in claim 1 wherein each said time period is controlled by a respective stimulation pulse produced by the pacemaker.

7. An arrangement as defined in claim 6 wherein the pacemaker includes a clock pulse generator for actuating stimulation pulses and said circuit is connected to have said time periods initiated by clock pulses from the clock pulse generator.

* * * * *